United States Patent
Hollis et al.

(10) Patent No.: US 8,600,701 B2
(45) Date of Patent: *Dec. 3, 2013

(54) DIVE COMPUTER WITH FREE DIVE MODE

(75) Inventors: Robert Hollis, San Leandro, CA (US); Michael S. Hollis, San Leandro, CA (US); Jack Calvin Holman, San Leandro, CA (US)

(73) Assignee: American Underwater Products, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/878,517

(22) Filed: Sep. 9, 2010

(65) Prior Publication Data

US 2011/0196643 A1  Aug. 11, 2011

Related U.S. Application Data

(63) Continuation of application No. 11/617,540, filed on Dec. 28, 2006, now Pat. No. 7,797,124.

(51) Int. Cl.
  *G01B 5/18*  (2006.01)
  *G01L 11/00*  (2006.01)

(52) U.S. Cl.
  USPC ...... 702/166; 128/204.22; 405/186; 702/138; 702/139

(58) Field of Classification Search
  USPC ......... 702/47, 50, 98, 138, 139, 166, 188, 23, 702/127; 128/204.22, 204.23, 210.27; 368/10, 11; 405/186; 73/865.1
  See application file for complete search history.

(56) References Cited

U.S. PATENT DOCUMENTS

| | | |
|---|---|---|
| 6,519,548 B1 | 2/2003 | Kuroda et al. |
| 6,842,402 B2 * | 1/2005 | Germiquet et al. ............. 368/10 |
| 6,931,348 B2 | 8/2005 | Furuta et al. |
| 7,144,198 B2 | 12/2006 | Hirose et al. |
| 7,383,150 B2 | 6/2008 | Angelini et al. |
| 7,698,091 B2 * | 4/2010 | Claude .......................... 702/139 |
| 7,797,124 B2 | 9/2010 | Hollis et al. |

OTHER PUBLICATIONS

Oceanic (Oceanic, GEO, Watch/Dive Computer Operating Manual, Doc No. 12-2734-r02, © 2002 Design, 2006, pp. 106-120).*
Stewart et al., "Diving Safety Manual", 2002, 58 pages.
"ATOM Operating Manual", Nov. 1, 2004, 152 pgs.
"Oceanic GEO Watch/Dive Computer Operating Manual", Doc No. 12-2734-r01, Oct. 20, 2006, 42 pgs.
"Oceanic GEO Watch/Dive Computer Operating Manual", Doc. No. 12-2734-r02, Apr. 26, 2007, 42 pgs.

* cited by examiner

*Primary Examiner* — John H Le
(74) *Attorney, Agent, or Firm* — KPPB LLP

(57) ABSTRACT

A dive computer with a free dive mode and/or wireless data transmission capabilities. In one embodiment the invention relates to a diving apparatus including a dive computer having a free dive mode, where the dive computer is configured to calculate a nitrogen loading in the free dive mode using a default value which is the fraction of oxygen in air, and where the free dive mode is used when a diver makes a dive without a self-contained underwater breathing apparatus. Another embodiment includes a method of operating a dive computer including recording two or more first identifiers, receiving pressure information from two or more pressure transmitters, the pressure information comprising second identifiers and pressure measurements, determining whether the pressure information contains one of the two or more first identifiers, and displaying a message indicative of the pressure information that contains one of the two or more first identifiers.

25 Claims, 10 Drawing Sheets

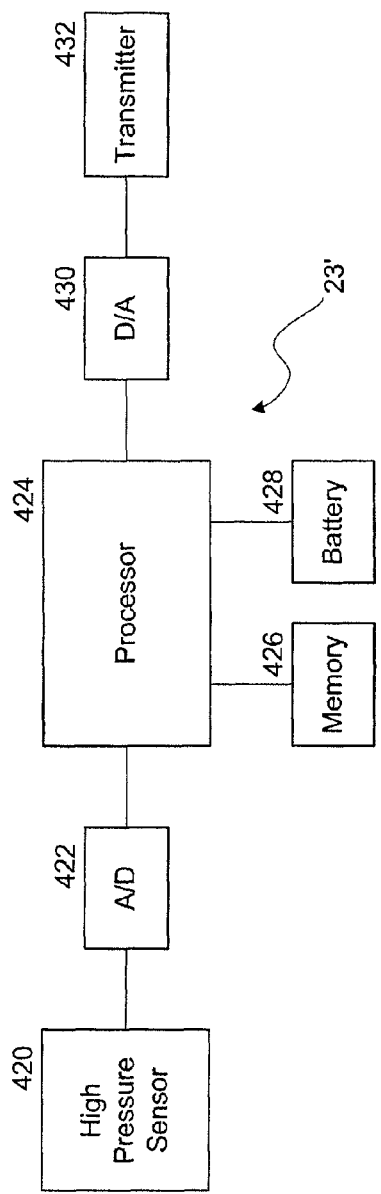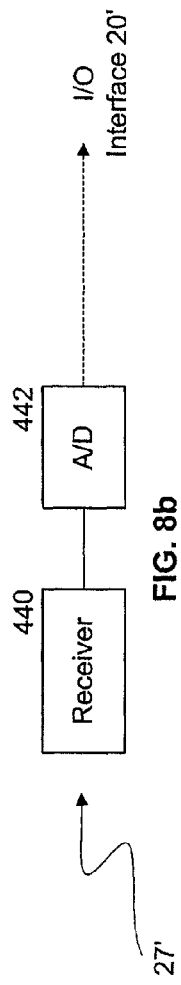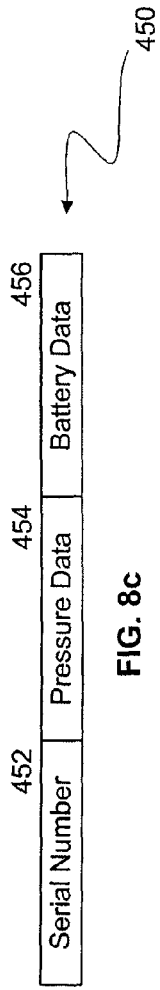

DIVE COMPUTER WITH FREE DIVE MODE

RELATED APPLICATION

The current application is a continuation application of application Ser. No. 11/617,540, Dec. 28, 2006, the disclosure of which is incorporated herein by reference.

FIELD OF INVENTION

The present invention relates generally to underwater exploration and more specifically to an apparatus and techniques for allowing free dives in conjunction with traditional underwater dives.

BACKGROUND OF THE INVENTION

The development of self-contained breathing systems has enabled humans to scuba dive and remain underwater for several hours. The ability to remain underwater for an extended period of time can enable divers to reach considerable depths and cover expansive distances in exploring underwater terrain. Dive computers can provide useful measurements and monitor critical factors for divers making such dives possible.

Divers often enjoy free diving. During a free dive, a diver does not use a self-contained breathing system but instead holds his/her breath. When considerable depths are reached during a free dive, the nitrogen loading of a diver can be impacted. To assist a diver who executes a free dive in conjunction with a traditional dive, dive computers generally include a feature that disables the dive computer for a period of time after a free dive. Disabling the dive computer is typically intended to discourage the diver from diving until the diver's nitrogen loading has returned to normal.

SUMMARY OF THE INVENTION

The present invention relates to a dive computer having a free dive mode. In one embodiment the invention relates to a diving apparatus including a dive computer having a free dive mode, where the dive computer is configured to calculate a nitrogen loading in the free dive mode using a default value which is the fraction of oxygen in air, and where the free dive mode is used when a diver makes a dive without a self-contained underwater breathing apparatus.

In another embodiment, the invention relates to a method of operating a dive computer including accepting an input specifying one or more modes of operation, where the one or more modes of operation comprises a free dive mode, and calculating a nitrogen loading in the free dive mode using the fraction of oxygen in air.

In yet another embodiment, the invention relates to a dive system including a pressure transmitter including a first pressure transducer connected to a processor unit, a transmitter connected to the processor unit, a memory connected to the processor unit, where the first pressure transducer is configured to measure pressure information, and where the transmitter is configured to transmit the pressure information to one or more dive computers, the one or more dive computers including a receiver configured to receive the pressure information from two or more pressure transmitters, a processor coupled to the receiver, and a display coupled to the processor, where the processor is configured to show pressure information on the display received from at least one of the two or more pressure transmitters.

In still yet another embodiment, the invention relates to a method of operating a dive computer including recording two or more first identifiers, where each first identifier is associated with a pressure transmitter, receiving pressure information from two or more pressure transmitters, the pressure information comprising second identifiers and pressure measurements, determining whether the pressure information contains one of the two or more first identifiers, and displaying the pressure information that contains one of the two or more first identifiers.

BRIEF DESCRIPTION OF THE DRAWINGS

FIG. 8a is a schematic illustration of an embodiment of the wireless pressure transducer of FIG. 7;

FIG. 8b is a schematic illustration of an embodiment of the receiver unit of the dive computer depicted in FIG. 7;

FIG. 8c is an illustration of a data packet that can be used with the dive computer and wireless pressure transducer of FIG. 7;

DETAILED DESCRIPTION OF THE INVENTION

Figure 1:
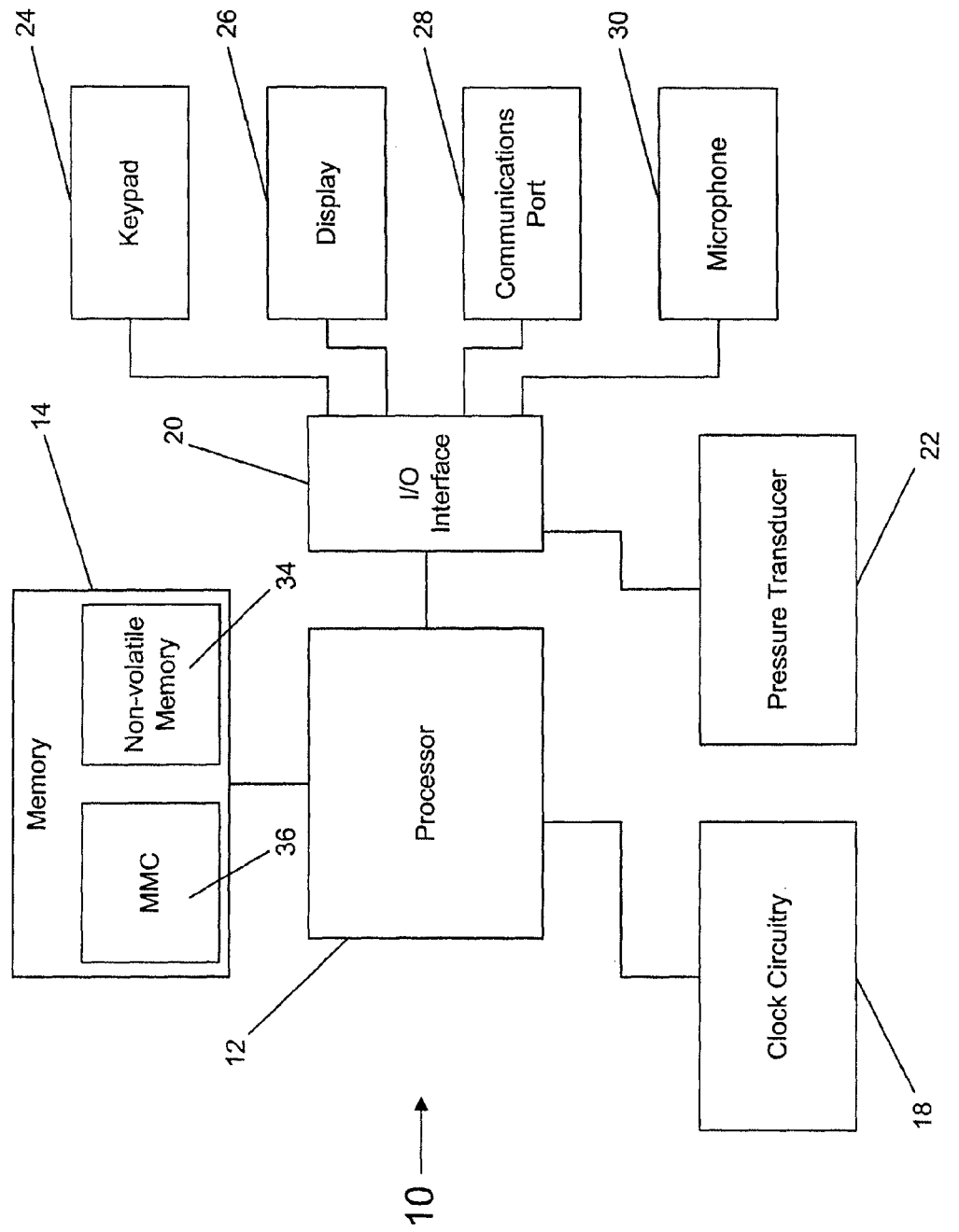
FIG. 1 is a schematic illustration of a dive computer in accordance with an embodiment of the present invention.

Referring now to the drawings, dive computers in accordance with embodiments of the present invention are illustrated. The dive computers can be placed in a plurality of modes, including a free dive mode, gauge mode and a normal dive mode. The normal mode can be used for general underwater scuba diving, while the gauge mode can be used by divers using an advanced breathing gas. The free dive mode can be used when a diver wishes to execute a dive without assistance from an external air supply and while holding his/her breath.

Dive computers in accordance with embodiments of the invention can calculate and store nitrogen loading in many modes, including the free dive mode. Once nitrogen loading has been calculated, dive computers can determine whether the calculated nitrogen loading is below default or diver specified thresholds. In the free dive mode, the dive computers can be operational following a free dive, enabling a diver to perform other dives without waiting for a predetermined period of time. The nitrogen loading calculated in the free dive mode can be carried over to the other modes of operation. In this way, the physiological effects of a free dive are accounted for in subsequent dives by the dive computer. Therefore, a diver can scuba dive after one or more free dives using dive computers in accordance with embodiments of the invention.

Dive computers in accordance with embodiments of the invention can be a part of sophisticated communication systems. Dive computers can be capable of communication with external devices using a variety of protocols and over wired or wireless mediums. In one embodiment, a dive computer can communicate with an external pressure transducer that monitors the pressure in the diver's tank and transmits information wirelessly to the dive computer. In such case, the dive computer can be worn on the wrist of the diver. The wireless pressure transducer can communicate pressure information to more than one dive computer so that a first diver can monitor the pressure of a second diver's tank as well as the pressure of his own dive tank. In some embodiments, the diver's mask can include a visual display and/or an audio device that communicates wirelessly with a hand held or wrist mounted dive computer.

Turning now to FIG. 1, a dive computer in accordance with an embodiment of the present invention is illustrated. The dive computer 10 includes a processor 12 that is connected to memory 14, clock circuitry 18 and an input/output interface 20. The input/output interface 20 is connected to a number of devices that can be used to communicate with a user or other devices. In the illustrated embodiment, these devices include a pressure transducer 22, a keypad 24, a display 26, a communications port 28 and a microphone 30.

A dive computer can include a number of functions which provide information to a diver. Dive computers can provide current depth, the maximum depth achieved during a dive, whether stop time will be required for decompression and if so, the number of stops along with the duration of those stops, dive time elapsed, water temperature, ascent or descent rate, air time remaining, gas pressure and approximate position. Dive computers often also provide warnings and user programmable thresholds for those warnings.

Although a particular embodiment of a dive computer is shown in FIG. 1, a free dive mode can be implemented and/or operated on any typical dive computer. A typical dive computer can include the necessary components or sensors to measure the parameters of a decompression algorithm. The parameters of a standard decompression algorithm are well known in the art and can include depth, pressure, and other parameters. Another parameter commonly included in a decompression algorithm is the gas mixture. The gas mixture typically includes oxygen, nitrogen, and some percentage of other gases. Decompression algorithms generally assume a standard or default gas mixture for diver consumption unless the diver specifies otherwise (i.e. a custom or user specified mixture).

Returning to FIG. 1, the processor 12 receives information from the clock circuitry 18, pressure transducer 22 and the input/output interface 20 and selectively stores the information in memory 14. In one embodiment, the processor is implemented using a MSP430F148 manufactured by Texas Instruments Incorporated of Dallas, Tex. However, the processor could be implemented using discrete logic components or several separate processing elements that share information.

The memory 14 can be used to store data logged by the dive computer 10, to temporarily store information during the performance of calculations and to store software used to control the operation of the processor 12. The memory 14 need not be a single integrated circuit and can be constructed from a number of integrated circuits having distinct properties. In the illustrated embodiment, the memory 14 includes non-volatile memory circuits 34 to store software for controlling the processor 12, manufacturer settings, user settings, calibration data and nitrogen loading. In addition, the memory 14 also includes a removable memory device 36 that is used to store data logged during a dive such as images, a dive profile, dive logs, nitrogen loading, audio recordings, and/or video games. The memory can also be connected to a digital camera (not shown) that is provided to enable the capture of images during a dive and to enable the use of these images as part of a dive log if desired by the user. In one embodiment, the removable memory device 36 is a flash memory card conforming to any number of standards such as MultiMediaCard or MMC standard.

The clock circuitry 18 can be used to measure the passage of time. Typically the clock circuitry 18 will incorporate a quartz crystal that is used to generate a periodic signal that can be observed in order to measure the passage of time. The clock circuitry 18 can also be synchronized with an external clock to enable time to be expressed in absolute terms using a time, a day, a month and a year. In one embodiment the clock circuitry is part of the MSP430F149 microcontroller described above.

The input/output interface 20 can be constructed from any variety of wires, antennas, transmitters, receivers, connectors and buffers. The configuration of the input/output interface 20 is dependent on the input/output devices that are connected to the dive computer. In the embodiment shown in FIG. 1, the input/output devices include a pressure transducer, a keypad, a display, a communications port and a microphone. In other embodiments, any other combination of input/output devices can be connected to the dive computer via the input/output interface. In one embodiment, the portion of the input/output interface connected to the pressure transducer includes a standard analog to digital converter. In another embodiment, the processor includes an analog to digital converter. In addition, the input/output interface uses a display driver such as an MSP430F4250 manufactured by Texas Instruments of Dallas, Tex. In some embodiments, analog content from the microphone 30 is converted to digital content by an analog to digital converter.

The pressure transducer 22 can be used to measure the pressure of the water in which the dive computer is immersed. In one embodiment a 17887.A Low Pressure Transducer manufactured by Pelagic Pressure Systems of San Leandro, Calif. can be used to construct the pressure transducer 22. In other embodiments, other components and/or circuitry capable of generating an electrical signal indicative of the water pressure in which the dive computer is immersed can be used.

A keypad 24 is typically provided to enable the user to enter information concerning the dive or to direct the processor 12 to provide the user with information. In one embodiment, the keypad 24 includes one or more buttons, toggles, joysticks or equivalent devices with which the user can provide instructions to the processor 12. In an exemplary embodiment, the diver can use the keypad to select the mode of operation, a threshold, or a calculation to display.

A display 26 is typically provided to present information in a graphical manner to the user. Information that can be provided to the user includes depth and/or time. If the dive computer 10 performs other functions, information relating to these functions can also be communicated using the display 26. In one embodiment, the display can provide information relating to the air time remaining. The air time remaining is the time that a diver can remain at the diver's current depth and still surface with the tank pressure reserve established during the diver's configuration of the dive computer. Air time remaining is calculated based on the diver's gas consumption and depth. In one embodiment, tank pressure can be measured once each second and an average rate of consumption is calculated over a ninety second period. This rate of consumption can then be used in conjunction with knowledge of the depth dependence to predict the breathing gas required for a safe ascent including any required compression stops.

In one embodiment, the display can provide information about the dive time remaining. The dive time remaining is the amount of time remaining before acceptable levels of nitrogen loading within the diver's body are exceeded, acceptable levels of oxygen accumulation are exceeded, or air time remaining decreases below an amount required to ascend. In one embodiment, the diver can specify a preferred nitrogen loading level. The time to fly is the amount of time that the diver should wait before riding in an airplane or driving to higher elevations. In one embodiment, the display can provide information about the desaturation time. The desaturation time can be defined as the theoretical time required for a diver's body to eliminate all residual nitrogen at sea level, and is based on the amount of nitrogen loading accumulated during a dive or set of repetitive dives.

Other input or output devices in addition to those described above can be connected to a dive computer in accordance with the present invention. In one embodiment, speakers are connected to the input/output interface to enable the playback of recorded speech, to allow a diver to listen to music during a dive or to provide an audible warning to the diver. In other embodiments, other combinations of devices can be used to meet the information requirements and data recording requirements of a diver during a dive.

As discussed previously, a dive computer can have several modes of operation. In one embodiment, a dive computer can have a normal mode, a gauge mode, and a free dive mode. In other embodiments, a dive computer can have a free dive mode and one or more other dive modes. In several embodiments, the dive computer performs a number of common functions, or functions that are performed during each dive mode.

Figure 2:
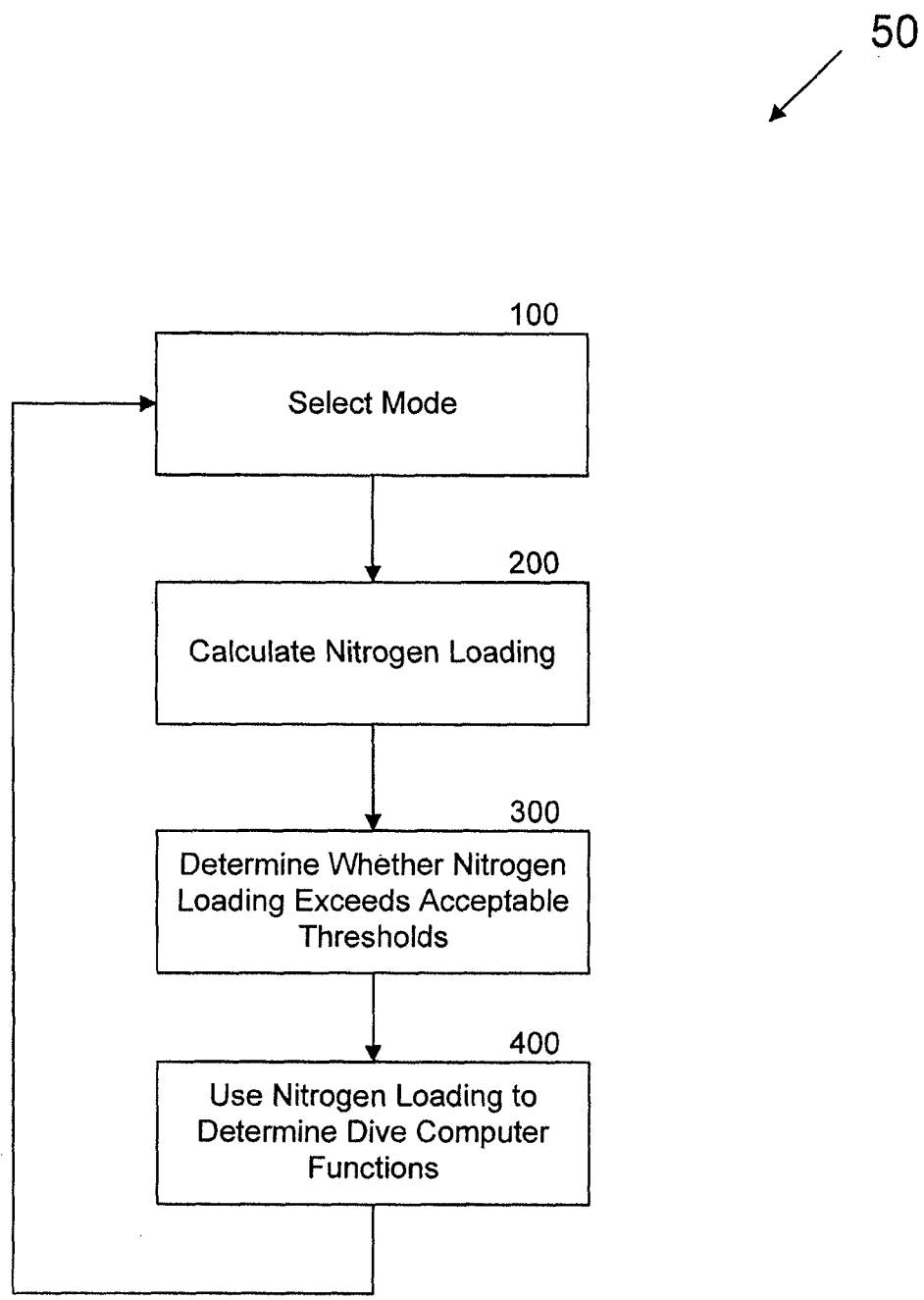
FIG. 2 is a flow chart illustrating a method of operating a dive computer in accordance with an embodiment of the present invention.

A flow chart illustrating a method of operating a dive computer in accordance with an embodiment of the present invention is shown in FIG. 2. The method 50 includes the steps of selecting (100) a mode of operation, calculating (200) nitrogen loading, determining (300) whether nitrogen loading exceeds acceptable thresholds, and using (400) the calculated nitrogen loading to determine dive computer functions. Dive computer functions associated with nitrogen loading can include air time remaining, dive time remaining, time to fly and desaturation time.

Figure 3:
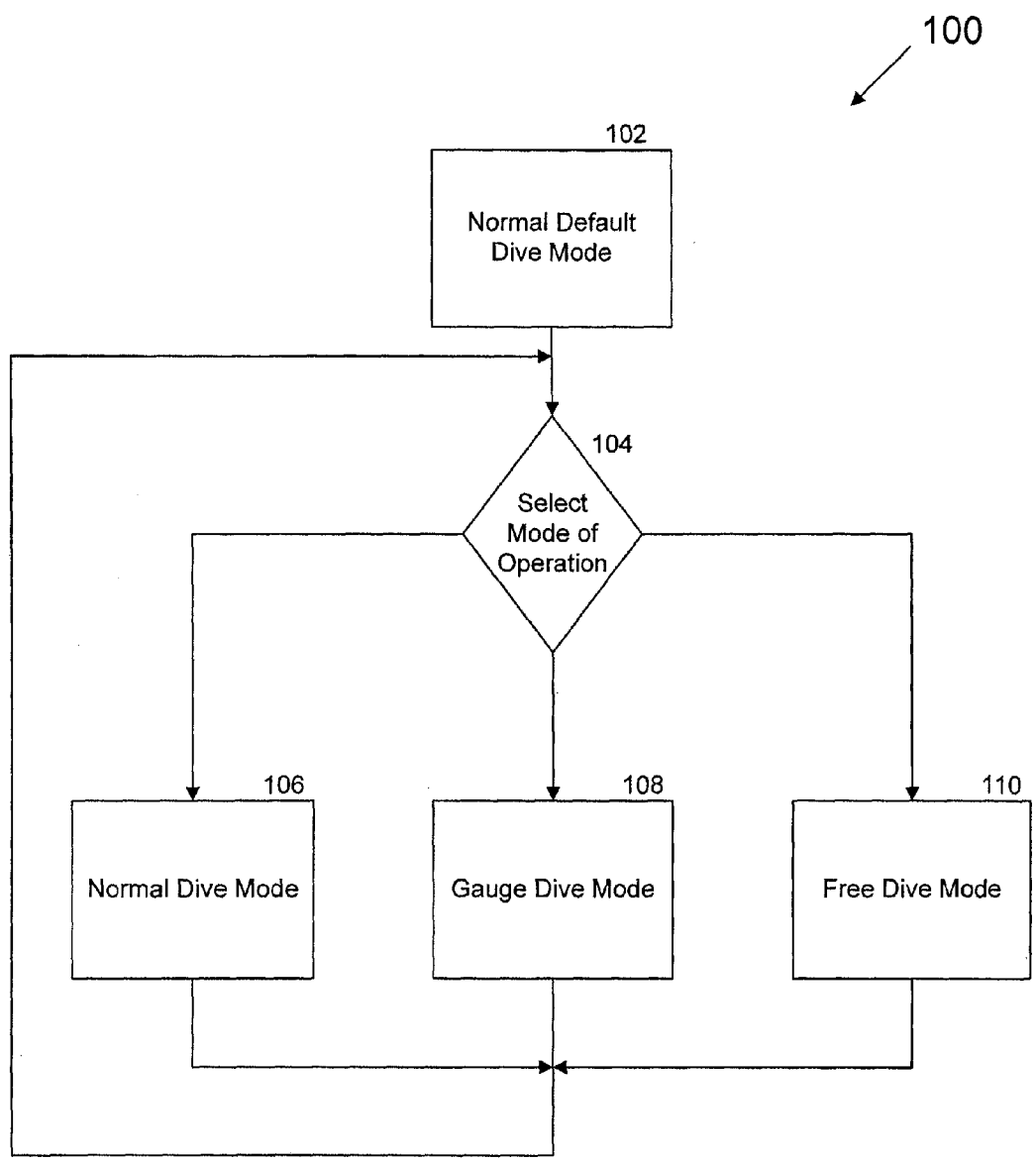
FIG. 3 is a flow chart illustrating a method of selecting a mode of operation for a dive computer in accordance with an embodiment of the present invention.

Dive computers can be placed in various modes by the diver depending on the type of dive to be executed. A flow chart illustrating a method for selecting a mode of operation for a dive computer in accordance with an embodiment of the present invention is shown in FIG. 3. In the method 100, the processor is placed (102) in a default mode in the illustrated example. The diver can then select (104) a mode of operation by pressing one or more buttons on the keypad (not shown). Depending on the one or more buttons pressed, the processor enters either a normal dive mode (106), a gauge dive mode (108), or a free dive mode (110). After the dive is performed, the diver can select (104) another mode of operation.

In other embodiments, the dive computer can have two or fewer modes, one of which is a free dive mode or its functional equivalent. In some embodiments, the dive computer can have more than three modes, including a free dive mode or its functional equivalent. In many embodiments, the modes can have different names but perform similar functions. In one embodiment, the default mode can be a mode other than the normal dive mode.

Figure 4:
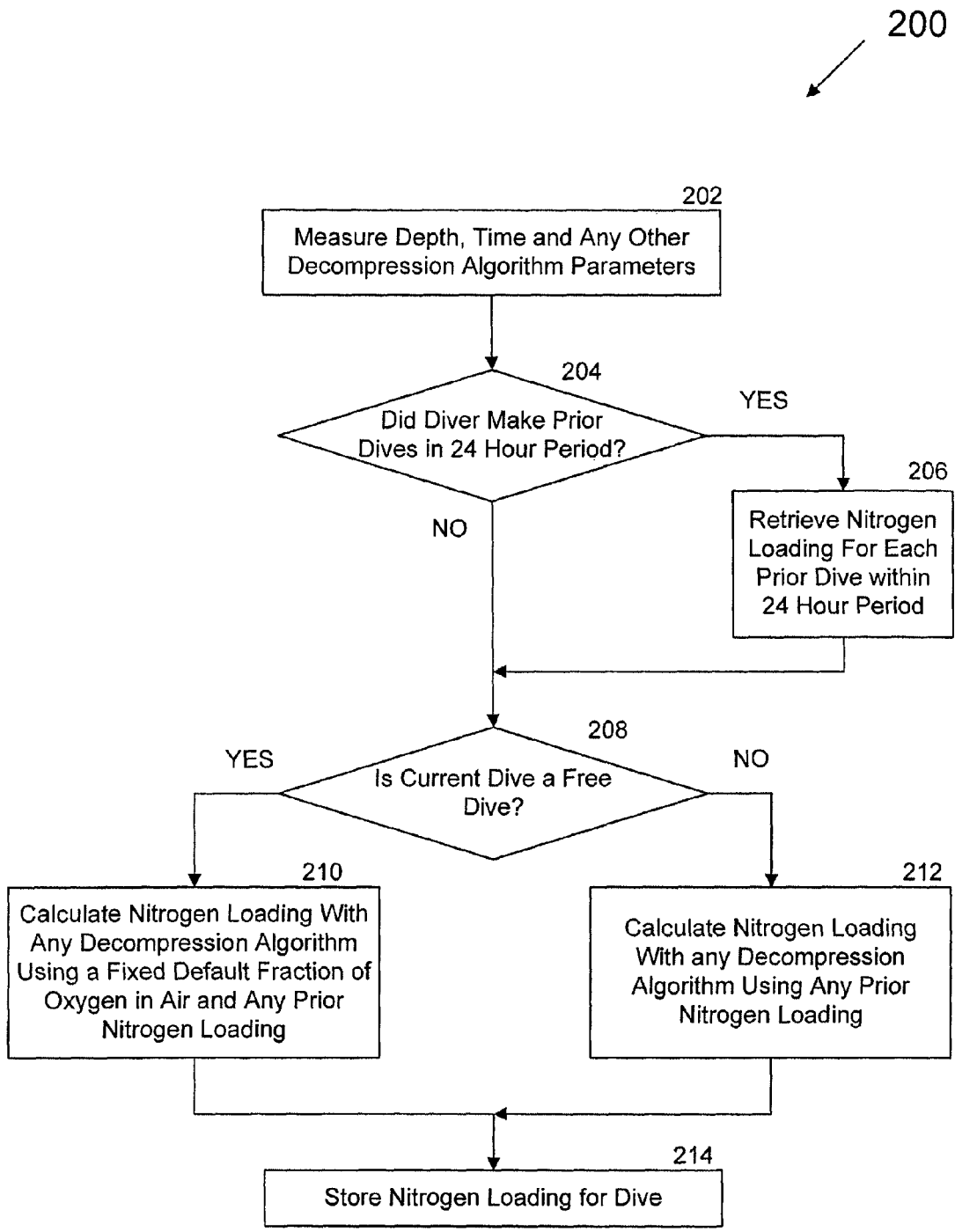
FIG. 4 is a flow chart illustrating a method of calculating nitrogen loading in accordance with an embodiment of the present invention.

In many of the dive modes, the dive computer makes calculations of nitrogen loading using a decompression algorithm. A number of techniques are known for calculating nitrogen loading. A flow chart illustrating a method of calculating nitrogen loading in accordance with an embodiment of the present invention is shown in FIG. 4. In the method 200, the processor measures (202) depth, time and other decompression algorithm parameters using one or more pressure transducers (not shown), the clock circuitry (not shown), or other sensors (not shown).

The processor then determines (204) whether or not the diver has made prior dives within a twenty four hour period. If the diver did make one or more dives, the processor retrieves (206) the residual nitrogen loading calculated for each dive within a twenty four hour time period and continues. Following nitrogen retrieval or if the diver did not make a prior dive, the processor then determines (208) whether or not the current dive is a free dive. If the current dive is a free dive, then the processor calculates (210) the nitrogen loading with a decompression algorithm using a fixed default value that is the fraction of oxygen in air, and any prior (i.e. residual) nitrogen loading within the twenty four hour period. In one embodiment, the fixed default value for the fraction of oxygen in air is set at twenty one percent. As previously discussed, decompression algorithms generally assume a standard or default gas mixture for diver consumption unless the diver specifies otherwise. In the free dive mode, the decompression algorithm uses a fixed default value that is the fraction of oxygen in the air at sea level. This is similar to according the diver the air he/she last breathed at the surface for a dive in the free dive mode. In several embodiments, the value is set based upon the altitude at which the dive commences to reflect the gas mix at that altitude. If the current dive is not a free dive, the processor calculates (212) the nitrogen loading using a decompression algorithm and any prior (i.e. residual) nitrogen loading within the twenty four hour period. After calculating nitrogen loading, whether in the free dive mode or not, the processor stores (214) the nitrogen loading calculated for the dive.

In one embodiment, a decompression algorithm such as the Buhlmann decompression algorithm can be used to calculate the nitrogen loading for a free dive. The Buhlmann decompression algorithm is discussed in U.S. Pat. No. 6,321,177 issued Nov. 20, 2001 to Ferrero et al. In other embodiments, decompression algorithms such as the varying permeability model or the reduced gradient bubble model can be used. Many decompression algorithms are based on the research of John Haldane and improvements commissioned by the DSAT (Diving Science and Technology) and PADI (Professional Association of Diving Instructors) organizations. Embodiments of the present invention can utilize one or more of these algorithms or any other algorithm that can be used to calculate nitrogen loading during a scuba dive.

In determining the decompression algorithm parameters, the processor can take into account other measurements. In one embodiment, the processor measures the pressure of compressed gases consumed by the diver during a dive. In several embodiments, the processor measures the rate of ascent or descent and/or the maximum depth. The decompression algorithm can be based on empirical data developed by Dr. Michael Powell in conjunction with the DSAT and PADI organizations. In one embodiment, the time period for checking for previous dives or retrieving the nitrogen loading can be more than or less than twenty four hours. In several embodiments, the prior nitrogen loading is calculated as a sum of all the nitrogen loading calculations for prior dives within a twenty four hour time period. In many embodiments, the processor stores the results of nitrogen loading calculations in the memory (not shown). In one embodiment, a single nitrogen loading calculation is stored that incorporates the nitrogen loading of all the previous dives in the given time period.

Figure 5:
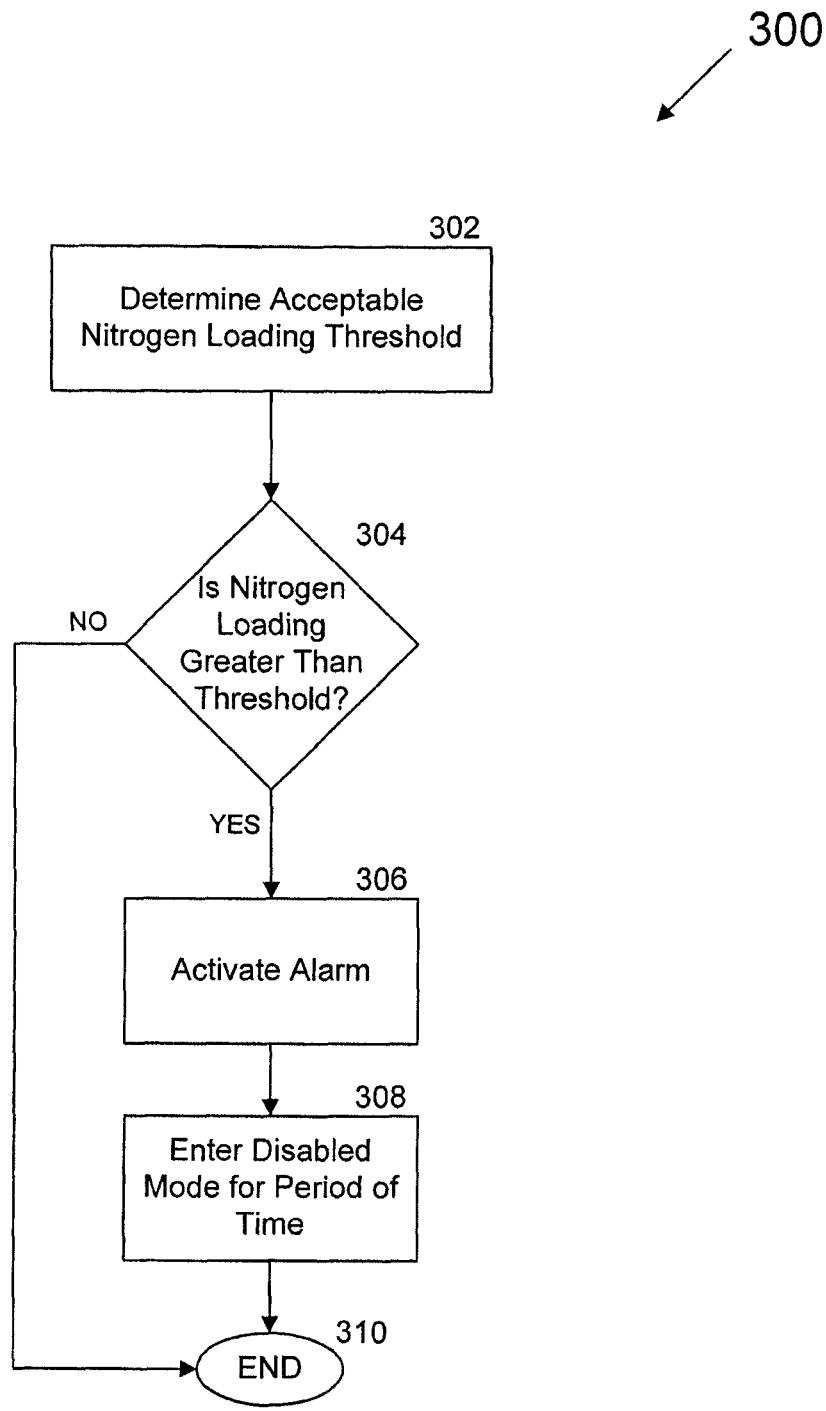
FIG. 5 is a flow chart illustrating a method of determining whether the nitrogen loading exceeds acceptable thresholds in accordance with an embodiment of the present invention.

As nitrogen loading is calculated, the dive computer can determine whether the nitrogen loading might be cause for alarm. A flow chart illustrating a method of determining whether the nitrogen loading exceeds acceptable thresholds for a free dive mode in accordance with an embodiment of the present invention is shown in FIG. 5.

In the method 300, the processor determines (302) an acceptable nitrogen loading threshold. The threshold can be a default value or a user specified value. The processor next checks (304) to see if the nitrogen loading is greater than the threshold. If the nitrogen loading is not greater than the threshold, then the process ends (310). If the nitrogen loading is greater than the threshold, then the processor activates (306) an alarm. After the alarm is activated and the dive computer has determined that the diver has returned to the surface with a level of nitrogen loading greater than the threshold, then the processor disables (308) the dive computer for a period of time. After the dive computer is disabled, the process ends (310).

In one embodiment, the dive computer is disabled for a period of twenty four hours. In other embodiments, the dive computer is disabled for a period greater than or less than twenty four hours which is determined to be an acceptable interval. In one embodiment, the processor can activate an alarm without entering a disabled mode. In several embodiments, the alarm can be a visual alarm such as a light emitting diode or LED, sequence of LEDs or other display. In many embodiments, the alarm can be an audio alarm or a combination of audio and visual warnings.

In other embodiments, the dive computer can determine whether the nitrogen loading exceeds acceptable thresholds for the gauge or normal dive modes. In these embodiments, the dive computer can determine acceptable nitrogen loading thresholds, give the diver instructions for completing decompression stops, account for completed decompression stops in nitrogen loading calculations, and decide whether to enter a disabled mode based upon the results of nitrogen loading calculations incorporating the effects of completed decompression stops. The functions performed in the gauge and normal dive computer modes that relate to determining whether nitrogen loading exceeds acceptable thresholds would be generally known to a skilled artisan.

Figure 6:
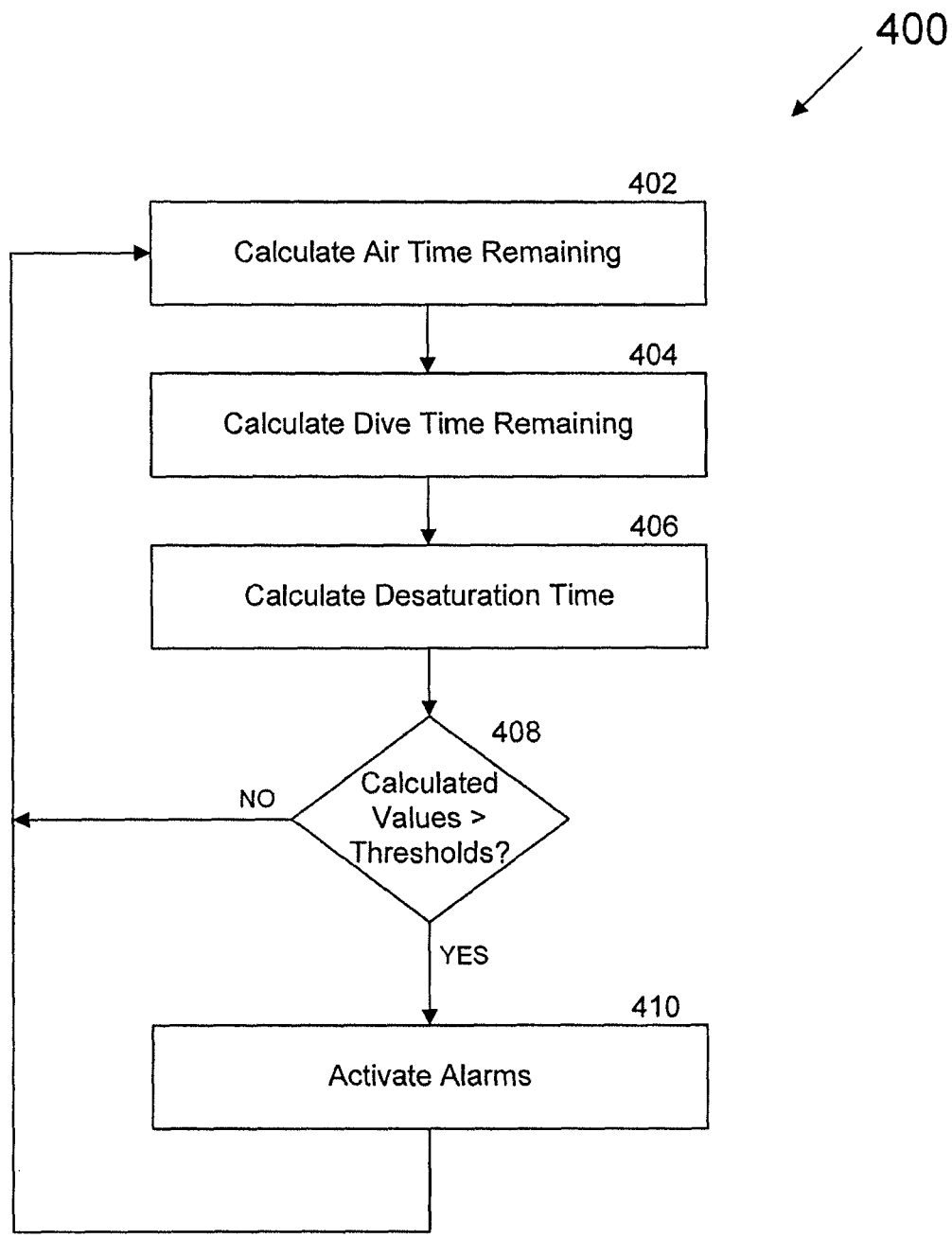
FIG. 6 is a flow chart illustrating a method of determining dive computer functions in accordance with an embodiment of the present invention.

After the nitrogen loading is calculated, the dive computer can use these values to calculate other dive computer functions. A flow chart illustrating a method of determining dive computer functions in accordance with an embodiment of the present invention is shown in FIG. 6. In the method 400, the processor calculates (402) the air time remaining. The processor calculates (404) the dive time remaining possibly using the calculated nitrogen loading. The processor calculates (406) the desaturation time using the calculated nitrogen loading. The desaturation time can be defined as the theoretical time required for a diver's body to eliminate all residual nitrogen at sea level.

The processor then checks (408) to see whether any of the calculated values are greater than their respective thresholds. The thresholds are default values unless the user has specified a particular value or percentage of the default value to be used instead. If any of the calculated values exceed their respective thresholds, then the processor activates (410) one or more alarms corresponding to the respective threshold exceeded. In many embodiments, audio and/or visual alarms can be activated as discussed previously. If none of the calculated values exceeds their respective thresholds or after activating the alarms, the processor returns to calculating the dive computer functions using nitrogen loading. In many embodiments, the calculations performed in 402, 404 and 406 may be performed in any order. In several embodiments, one or more of the calculations (i.e., dive time remaining) may not be performed until the diver requests the calculation by pressing an input key on the dive computer.

Divers engaging in free diving often follow a free dive with a second free dive or a dive using a self-contained underwater breathing apparatus (scuba dive). This is commonly referred to as repetitive diving. The U.S. Navy tables, which are known to one skilled in the art, describe empirical guidelines for making repetitive dives. The diving tables require a diver to stop for at least ten minutes at the surface (surface interval time) before beginning a second dive. If the diver does not have a surface interval time of at least ten minutes, it is not treated as a repetitive dive. It is instead treated as a single dive. Although the invention is not bound by theory, it is thought that the dive tables offer more favorable (i.e. longer) bottom times for repetitive dives than for a single dive. This thought is supported by the fact that the longer the diver spends at the surface, the more nitrogen he releases from his blood.

In accordance with one embodiment of the invention, dive computers having a free dive mode can allow a diver who has completed a free dive to make a second dive that is treated by the dive computer as a repetitive dive after just one minute of surface interval time. In this case, the second dive, which can be either a free dive or a scuba dive, is treated by the dive computer as a repetitive dive for the purpose of calculating the maximum dive time possible without decompression stops, nitrogen loading, oxygen loading and/or other parameters relevant to performing single or repetitive dives. In other embodiments, the dive computers can allow a diver who has completed a free dive to make a second dive that is treated by the dive computer as a repetitive dive after two minutes or after five minutes. Although the invention is not bound by theory, it is thought that the deviation from the diving table is possible since the diver is not breathing compressed gas during the free dive. The diver instead breathes the air he acquired at the surface.

Figure 7:
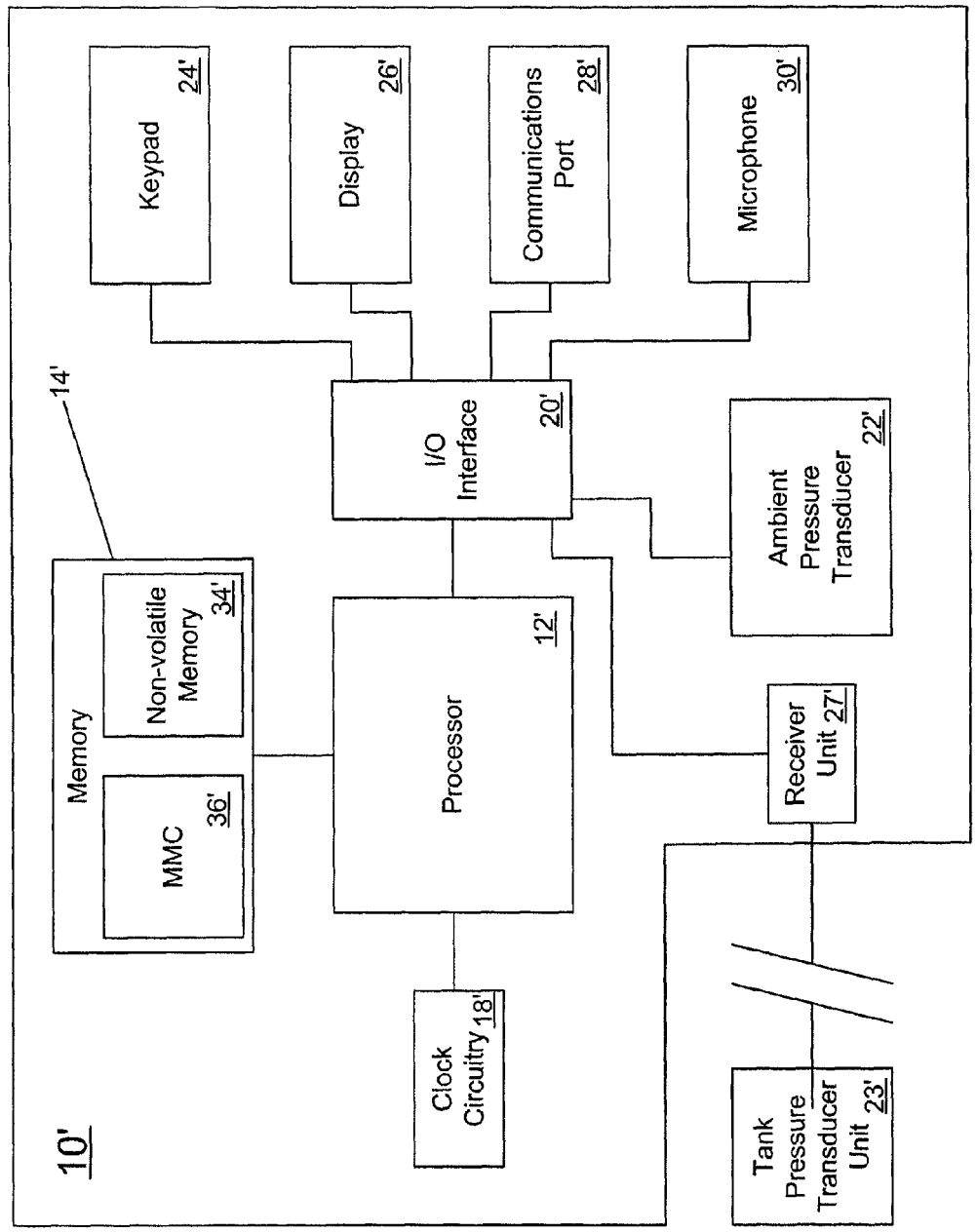
FIG. 7 is a schematic illustration of an embodiment of a dive computer and a wireless tank pressure transducer unit in accordance with an embodiment of the present invention.

A pressure transducer that can broadcast pressure related information to more than one diver can greatly assist divers when two or more divers are diving together. A schematic illustration of an embodiment of a dive computer and a wireless pressure transducer in accordance with an embodiment of the present invention is shown in FIG. 7. In one embodiment, the wireless pressure transducer can be located on a tank used by the diver (i.e. tank pressure transducer unit). The dive computer 10' includes a processor 12' that is connected to memory 14', clock circuitry 18' and an input/output interface 20'. The input/output interface 20' is connected to a number of devices that can be used to communicate with a user or other devices. In the illustrated embodiment, these devices include an ambient pressure transducer 22', a keypad 24', a display 26', a receiver unit 27', a communications port 28' and a microphone 30'. In another embodiment, the receiver unit 27' can be connected directly to the processor 12'. The operation of these dive computer components except for the receiver unit 27' is described previously in the discussion of FIG. 1. In the illustrated embodiment, the ambient pressure transducer 22' can measure the depth of the diver and the tank pressure transducer unit 23' can measure the pressure of the gas in the diver's tank.

In operation, the tank pressure transducer unit 23' can communicate with the receiver unit 27' of the dive computer. The tank pressure transducer unit 23' is capable of transmitting data via various protocols and methods. In many embodiments, the tank pressure transducer unit can communicate with the dive computer via a wireless or wired communication link. In one embodiment, wireless communication can be achieved using a communication system that complies with the Bluetooth, or IEEE 802.15.1, standard. In another embodiment, wireless communication can be achieved using one or more piezoelectric devices. In one or more embodiments, communication can be achieved using magnetic fields and techniques such as pulse width modulation. In other embodiments, the wireless communication can be achieved using other protocols and methods.

A schematic illustration of an embodiment of the tank pressure transducer unit of FIG. 7 is shown in FIG. 8a. In this embodiment, the tank pressure transducer unit can act as a wireless pressure transducer. In other embodiments, the tank pressure transducer is connected to the dive computer using a wired connection. The wireless pressure transducer 23' includes a high pressure sensor 420, an analog to digital converter (A/D) 422, a processor 424, a memory 426, a battery 428, a digital to analog converter (D/A) 430 and a transmitter 432. The processor 424 is connected to the A/D 422, memory 426, battery 428 and D/A 430. The A/D 422 is connected to the high pressure sensor 420. The D/A 430 is connected to the transmitter 432.

In operation, the high pressure sensor measures the pressure of gas in the diver's tank (not shown) and outputs the pressure information to the A/D. The A/D converts the analog pressure information received from the high pressure sensor into digital information and outputs it to the processor. The processor can store the digital pressure information in the memory. The memory can also store information unique to the wireless pressure transducer like a serial number. The processor can receive information from the battery regarding the status of the battery and/or the amount of time remaining before the battery is exhausted. The processor can assemble packets of information 450 including the serial number 452, pressure data 454, and battery data 456 as shown in FIG. 8c. In other embodiments, different formats of packets can be used where the packets include information related to pressure and a serial number.

The processor can output the data packets to the D/A. The D/A can include a pulse generator capable of encoding data packets using pulse width modulation. The pulse width modulated packets can be sent to the transmitter. In one embodiment, the transmitter can include a buffer or temporary memory for storing packets. The transmitter can include a coil capable of sending the pulse width modulated packets using a magnetic field.

In other embodiments, the wireless pressure transducer is capable of communicating using other wireless protocols. In such embodiments, other components and/or additional components are used to implement the wireless communication.

An embodiment of the receiver unit of the dive computer shown in FIG. 7 is shown in FIG. 8b. The receiver unit 27' includes a receiver 440 and an analog to digital converter (A/D) 442. The receiver can include amplifiers, filters and/or coils appropriate to receive a magnetic field as known to a skilled artisan. The receiver 440 is connected to the A/D 422 which is connected to the I/O interface 20' (not shown). In another embodiment, the A/D is connected directly to the processor 12' (not shown).

In operation, the receiver receives the pulse width modulated packets in the form of a magnetic field. The receiver can use a coil to receive the magnetic field and produce a corresponding analog signal. The receiver outputs the analog signal to the A/D. The A/D can reconstruct digital packets from the pulse width modulated signal. The A/D can include a memory for storing the received information (i.e. packets). The A/D can output received packets in digital form to the I/O interface 20'. In other embodiments, the A/D can output digital information directly to the processor 12' (see FIG. 7).

The processor 12' can compare the serial number 452 of each digital packet 450 received to identification/serial numbers stored in memory. In one embodiment, the diver has entered the stored identification/serial numbers into the memory of the dive computer. In the event that the stored serial number does not match the serial number contained in the received packet, the processor can discard the packet.

In one embodiment, collisions of signals or interference from signals sent by multiple wireless pressure transmitters is avoided by configuring each wireless pressure transmitter with a timing sequence. The timing sequence can specify a particular period of time for each wireless pressure transmitter to transmit. In this way, transmitters are generally transmitting at different times so that collisions and/or interference between transmitters is avoided.

In other embodiments, the receiver unit is capable of communicating using other wireless protocols. In such embodiments, other components and/or additional components are contemplated to implement the wireless communication.

Figure 9:
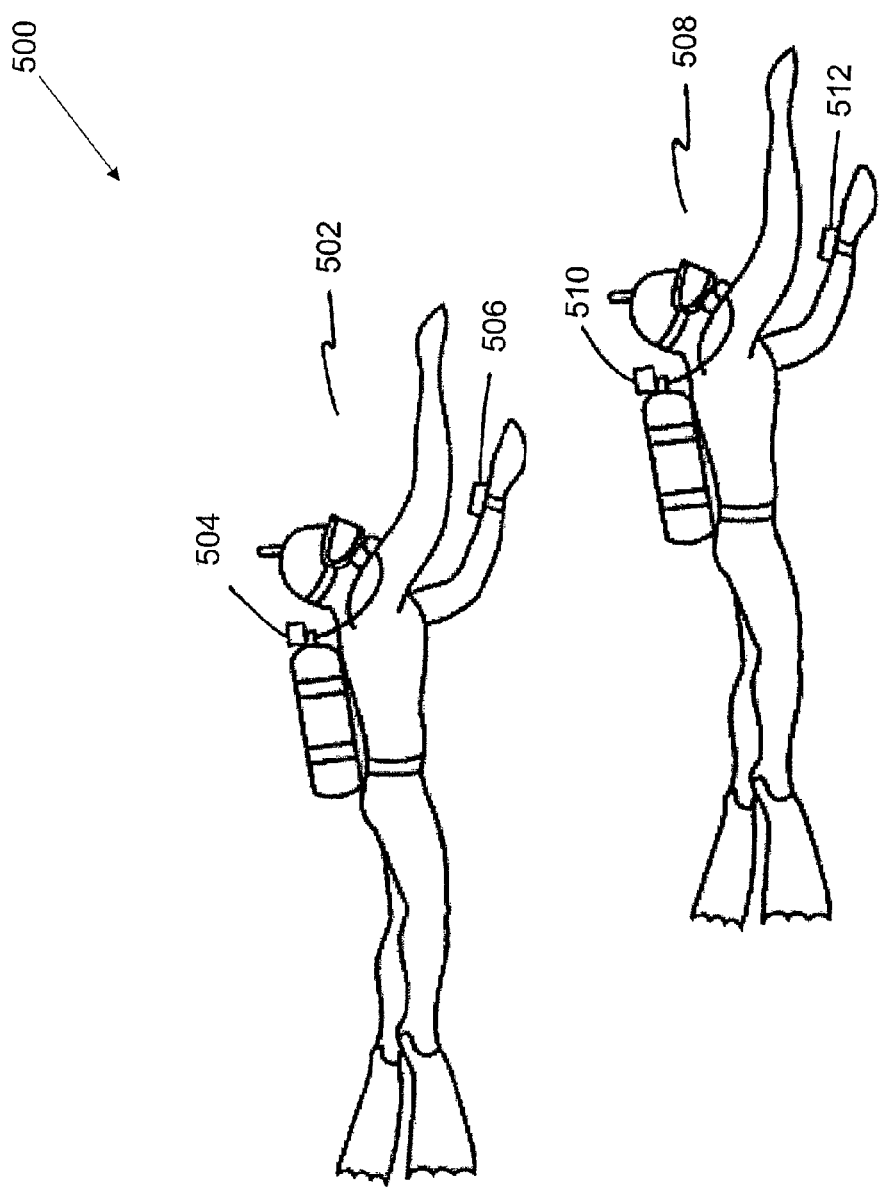
FIG. 9 is a side view of a communication system illustrating two divers using wireless pressure transducers and dive computers in accordance with embodiments of the present invention.

Wireless communication can be quite useful as divers often dive in groups of two or more. A side view of a communication system illustrating two divers using wireless pressure transducers and dive computers in accordance with embodiments of the present invention is shown in FIG. 9. The system includes a first diver 502 and a second diver 508. Communication system components attached to the first diver 502 include a first dive computer 506 and a first wireless pressure transducer 504. Communication system components attached to the second diver 508 include a second dive computer 512 and a second wireless pressure transducer 510.

The dive computers 506 and 512 can be wrist mountable. The wireless pressure transducers 504 and 510 can be mounted to the regulator first stage located on the upper portion of the diver's tank. In another embodiment, the wireless pressure transducers (WPTs) can be mounted in proximity to the tank by any appropriate attachment means.

Figure 10:
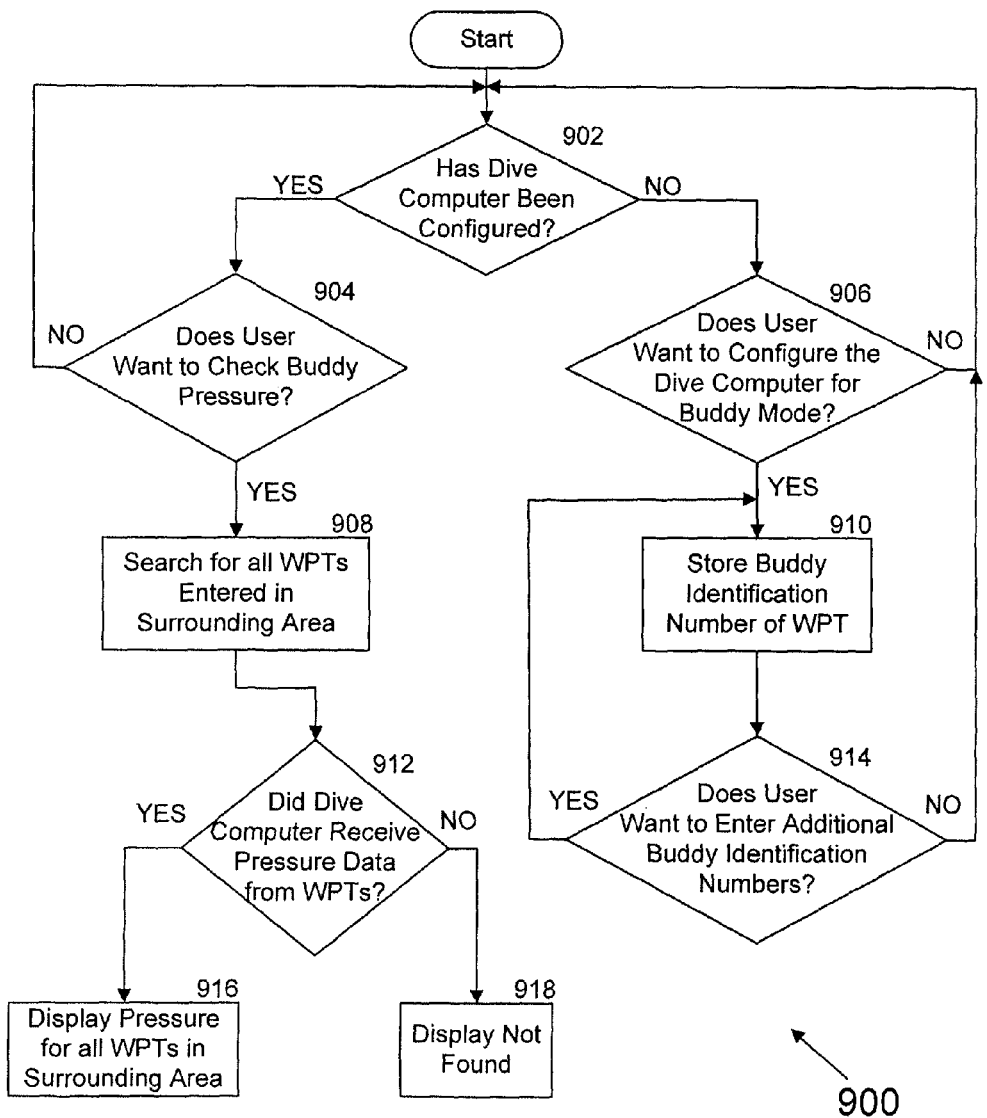
FIG. 10 is a flow chart illustrating a method of operating a dive computer that includes a wireless pressure transducer in accordance with an embodiment of the present invention.

The communication system of FIG. 9 can operate in a number of ways. A flow chart illustrating a method of operating a dive computer that includes a wireless pressure transducer in accordance with an embodiment of the present invention is shown in FIG. 10. In the method 900, the dive computer can determine (902) whether it has been configured for wireless communication with a wireless pressure transducer (WPT). In one embodiment, the dive computer determines whether or not it has been configured by checking its memory to see if the identification numbers of any WPTs have been stored.

In the event that the dive computer has not been configured, the dive computer determines (906) whether or not the diver wants to configure the dive computer for communication with a WPT, or "buddy mode." If the diver indicates that he wants to configure the dive computer, then the dive computer responds by storing (910) the identification number of the WPT that the diver wishes to monitor. If the diver indicates that he does not want to configure the dive computer, then the dive computer returns to determining (902) if the dive computer has been configured. After storing the identification or serial number, the dive computer determines (914) whether the user wants to enter additional WPT identification numbers. If the user indicates a desire to enter additional identification numbers, then the dive computer responds by storing (910) the identification number of the WPT entered by the user. In the event that the user does not want to enter additional identification numbers, the dive computer returns to determining (902) if the dive computer has been configured.

In the event that the dive computer has been configured, the dive computer determines (904) whether or not the user wants to check buddy pressure, or the pressure of WPTs that are configured for being monitored. If the user does not want to check buddy pressure, then the dive computer returns to checking (902) to see if the dive computer has been configured. If the user presses a key indicating that the diver wants to check buddy pressure, the dive computer searches (908) for all WPTs in the area surrounding the dive computer. In one embodiment, the dive computer can receive the transmissions of all the WPTs within a radius of five feet. In another embodiment, the dive computer can receive the transmissions of all the WPTs within a radius of ten feet. In yet another embodiment, the dive computer can receive the transmissions of all the WPTs within a radius greater than ten feet. After searching for WPTs, the dive computer can determine (912) whether it received pressure data from any WPTs from which it was configured to receive data. If the dive computer received pressure data, the dive computer displays (916) the pressure data for all WPTs from which it received pressure data. In the event that the dive computer did not receive pressure data, the dive computer displays a message indicating that the pressure or buddy pressure was not found. In one embodiment where the dive computer receives pressure data from at least one of the WPTs from which it was configured to receive data, the dive computer displays a message indicative of the pressure data for at least one of the WPTs from which the dive computer received pressure data. In such case, the message can include an icon, symbol or text message indicative of the pressure data or a warning based on the pressure data. In one embodiment, the dive computer can display the pressure data for at least one of the WPTs from which the dive computer received pressure data.

The WPTs can operate by transmitting pressure information wirelessly. In one embodiment, the transmitted information can include a unique identification number such as a serial number and the pressure of the tank which is being monitored by the WPT. In another embodiment, only pressure information is transmitted. In several embodiments, the information can be transmitted wirelessly using a system that conforms to the Bluetooth, or IEEE 802.15.1, standard. In another embodiment, the information can be transmitted wirelessly using one or more piezoelectric devices. In one or more embodiments, communication can be achieved using magnetic fields and techniques such as pulse width modulation. In other embodiments, other wireless protocols or communication systems can be used. In one embodiment, the dive computer can detect one or more WPTs in the vicinity of the dive computer and configure itself by storing the identification numbers of the detected WPTs. This can be useful for configuring "buddy mode" before a dive.

The wireless pressure transmitters can be used by a single diver or two divers as in the embodiment shown in FIG. 9. In other embodiments, more than two divers can configure their dive computers to monitor the pressure of one or more of the other divers on a particular dive. The dive computers capable of monitoring the pressure of other divers tanks can be hand held devices, wrist mounted, or otherwise mounted to the diver's person.

Variations, modifications, and other implementations of what is described herein will occur to those of ordinary skill in the art without departing from the spirit and the scope of the invention as claimed. Although the invention has been described with respect to certain embodiments, it should be recognized that the invention includes the claims and their equivalents supported by this disclosure. In many embodiments, a user can specify nominal values for thresholds or a percentage of default values for thresholds. In one embodiment, the percentage may be set such that the thresholds are equivalent to their default values if the diver were diving at 3,000 feet elevation. In several embodiments, a user can specify more conservative thresholds. In other embodiments, a user can specify more aggressive thresholds. In some embodiments, a user cannot specify thresholds that are more aggressive than the default values.

What is claimed is:

1. A diving apparatus comprising:
a dive computer having a free dive mode;
wherein the dive computer is configured to calculate a nitrogen loading in the free dive mode using a default value which is the fraction of oxygen in air; and
wherein the free dive mode is used when a diver makes a dive without a self-contained underwater breathing apparatus.

2. The diving apparatus of claim 1, wherein the dive computer is configured to compare a threshold with the calculated nitrogen loading.

3. The diving apparatus of claim 2, wherein the dive computer is configured to activate an alarm based on the comparison of the threshold and the calculated nitrogen loading.

4. The diving apparatus of claim 1, wherein the dive computer is configured to calculate the nitrogen loading in the free dive mode using the default value and a residual nitrogen loading.

5. The diving apparatus of claim 4, wherein the residual nitrogen loading is a sum of nitrogen loading calculations made over a prior time period.

6. The diving apparatus of claim 1, wherein the dive computer comprises:
a processor;
a pressure transducer connected to the processor;
a display connected to the processor; and
clock circuitry connected to the processor;
wherein the processor is configured to determine time using the clock circuitry;
wherein the processor is configured to determine depth of submersion using the pressure transducer; and
wherein the processor is configured to provide depth and time information using the display.

7. The diving apparatus of claim 1, wherein the dive computer is configured to calculate at least one of air time remaining, dive time remaining and desaturation time, the calculation based on the nitrogen loading.

8. The diving apparatus of claim 1, wherein the dive computer is configured to allow the diver to perform a second dive that is treated as a repetitive dive following a dive without a self-contained underwater breathing apparatus after thirty seconds.

9. The diving apparatus of claim 1, wherein the dive computer is configured to allow the diver to perform a second dive that is treated as a repetitive dive following a dive without a self-contained underwater breathing apparatus after one minute.

10. The diving apparatus of claim 1, wherein the dive computer is configured to allow the diver to perform a second dive that is treated as a repetitive dive following a dive without a self-contained underwater breathing apparatus after two minutes.

11. The diving apparatus of claim 1, wherein the dive computer is configured to allow the diver to perform a second dive that is treated as a repetitive dive following a dive without a self-contained underwater breathing apparatus after five minutes.

12. The diving apparatus of claim 1:
wherein the dive computer has a normal dive mode;
wherein the dive computer is configured to calculate nitrogen loading in the normal dive mode accounting for use of a self-contained breathing apparatus; and
wherein the dive computer is configured to allow a dive in the free dive mode following a dive in the normal dive mode.

13. The diving apparatus of claim 1:
wherein the dive computer has a normal dive mode;
wherein the dive computer is configured to calculate nitrogen loading in the normal dive mode accounting for use of a self-contained breathing apparatus; and
wherein the dive computer is configured to allow a dive in the normal dive mode following a dive in the free dive mode.

14. A method of operating a dive computer comprising:
accepting an input specifying one or more modes of operation using a dive computer, wherein the one or more modes of operation comprises a free dive mode, wherein the free dive mode is used when a diver makes a dive without a self-contained underwater breathing apparatus; and
calculating a nitrogen loading in the free dive mode using the fraction of oxygen in air and the dive computer.

15. The method of claim 14, wherein the nitrogen loading calculation is a function of a residual nitrogen loading.

16. The method of claim 14, further comprising comparing the calculated nitrogen loading to a threshold using the dive computer.

17. The method of claim 16, further comprising activating an alarm based on the comparison of the calculated nitrogen loading to the threshold using the dive computer.

18. The method of claim 14, further comprising using the calculated nitrogen loading to calculate air time remaining, dive time remaining and/or desaturation time using the dive computer.

19. The method of claim 14, further comprising:
determining a time using a clock circuitry;
determining a depth of submersion using a pressure transducer; and
displaying the depth and time using the dive computer.

20. The method of claim 14, further comprising allowing a diver to perform a second dive that is treated as a repetitive dive following a dive without a self-contained underwater breathing apparatus after thirty seconds using the dive computer.

21. The method of claim 14, further comprising allowing a diver to perform a second dive that is treated as a repetitive dive following a dive without a self-contained underwater breathing apparatus after one minute using the dive computer.

22. The method of claim 14, further comprising allowing a diver to perform a second dive that is treated as a repetitive dive following a dive without a self-contained underwater breathing apparatus after two minutes using the dive computer.

23. The method of claim 14, further comprising allowing a diver to perform a second dive that is treated as a repetitive dive following a dive without a self-contained underwater breathing apparatus after five minutes using the dive computer.

24. The method of claim 14, where the one or more modes further comprise a normal dive mode, the method further comprising:
calculating a nitrogen loading in the normal dive mode using the dive computer, the calculation accounting for use of a self-contained breathing apparatus; and
allowing a dive in the free dive mode following a dive in the normal dive mode using the dive computer.

25. The method of claim 14, where the one or more modes further comprise a normal dive mode, the method further comprising:
calculating a nitrogen loading in the normal dive mode using the dive computer, the calculation accounting for use of a self-contained breathing apparatus; and
allowing a dive in the normal dive mode following a dive in the free dive mode using the dive computer.

* * * * *